| United States Patent [19] | [11] 4,044,151 |
|---|---|
| Comer et al. | [45] Aug. 23, 1977 |

[54] SULFAMIDOPHENETHANOLAMINE THERAPEUTIC PROCESS

[75] Inventors: William T. Comer; John D. Catt, both of Evansville, Ind.

[73] Assignee: Mead Johnson & Company, Evansville, Ind.

[21] Appl. No.: 633,537

[22] Filed: Nov. 19, 1975

Related U.S. Application Data

[62] Division of Ser. No. 399,024, Sept. 20, 1973, Pat. No. 3,923,886.

[51] Int. Cl.$^2$ .................... A61K 31/18; A61K 31/44; A61K 31/445
[52] U.S. Cl. .................................. 424/321; 424/263; 424/267

[58] Field of Search ............... 424/321, 246, 248, 263, 424/274, 267

[56] References Cited

U.S. PATENT DOCUMENTS 3,711,545  1/1973  Kaiser et al. .................... 260/556 N

OTHER PUBLICATIONS

Uloth et al., J. Med. Chem., 9:88–97, (1966).

Primary Examiner—Albert T. Meyers
Assistant Examiner—Daren M. Stephens
Attorney, Agent, or Firm—R. H. Uloth; R. E. Carnaham

[57] ABSTRACT para-Sulfamidophenethanolamines are prepared from para-sulfamidophenacyl halides. The phenethanolamines have useful beta-adrenergic blocking action.

7 Claims, No Drawings

SULFAMIDOPHENETHANOLAMINE THERAPEUTIC PROCESS

CROSS REFERENCE TO RELATED APPLICATION

This application is a divisional application of our co-pending application Ser. No. 399,024 filed Sept. 20, 1973, and now U.S. Pat. No. 3,923,886 patented Dec. 2, 1975.

FIELD OF THE INVENTION

This invention is concerned with a method for inhibiting mammalian beta-adrenergic activity which involves dosing with a carbocyclic amide of a sulfonic acid. Specifically, active ingredients are phenethanolamines bearing a sulfamide group on the benzene ring.

DESCRIPTION OF THE PRIOR ART

Various arylakylsulfamides, aryloxyalkylsulfamides, indanylsulfamides, and sulfamylaminomethylene malonates have been described in the literature as being useful as synthetic medicinals. The utilities of these prior substances lie almost exlusively in their action on the central nervous system including tranquilizer, sedative, and anticonvulsant action. None of these substances is a phenethanolamine bearing a sulfamido group on the benzene ring, nor do they have utility as adrenergic blocking agents. Refer for example to U.S. Pat. Nos. 3,143,549, 3,373,184, 3,383,414, and 3,406,174. Some sulfonanilides in the phenethanolamine series are described in U.S. Pat. No. 3,341,584.

SUMMARY OF THE INVENTION

This invention is concerned with a novel group of sulfamides having the following structural formula

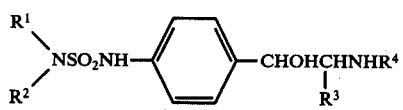

Formula I and the pharmaceutically acceptable acid addition and metal salts thereof. In this formula, the following definitions are intended for the substituents referred to by the symbols $R^1$, $R^2$, $R^3$, and $R^4$. $R^1$ is hydrogen, lower alkyl having from 1 to 4 carbon atoms, cyclopropyl, phenyl, or tolyl. $R^2$ is hydrogen, lower alkyl having from 1 to 4 carbon atoms, cyclopropyl, or benzyl. $R^1$ and $R^2$ may be connected to one another or through an oxygen or sulfur atom to form with the sulfamide nitrogen atom at five or six membered heterocyclic group such as piperidine, pyrrolidine, or morpholine. $R^3$ is hydrogen, methyl, or ethyl. $R^4$ is hydrogen, cyclopropyl, or lower alkyl having from 1 to 4 carbon atoms.

In the foregoing definitions, the lower alkyl group referred to as having from 1 to 4 carbon atoms may have a straight or branched chain illustrated by methyl, ethyl, n-propyl, isopropyl, tert.-butyl, sec.-butyl, or isoburtyl. Preferred compounds are those in which $R^1$ and $R^2$ are hydorgen or methyl, $R^3$ is hydrogen, and $R^4$ is a branched chain alkyl group having 3 or 4 carbon atoms such as isopropyl or tert.-butyl.

The compounds of this invention have adrenergic blocking action which is selective for the beta-adrenergic receptors, and reduce blood pressure when administered systemically to mammals. beta-Adrenergic blocking agents have been used in the treatment of various forms of heart disease including angina pectoris, cardiac arrhythmias, and hypertension, and have also been suggested for the treatment of anxiety neurosis and metabolic disorders such as hyperlactacidemia, hyperglycemia, and ketosis. Preferred compounds of the present invention are those substances of the above formula wherein $R^4$ is isopropyl and $R^1$, $R^2$, and $R^3$ are either hydrogen or methyl.

The most preferred compounds are N,N-dimethyl-N'-[4-(1-hydroxy-2-isopropylaminoethyl)phenyl]sulfamide and N-[4-(1-hydroxy-2-isopropylaminoethyl)phenyl]-sulfamide and the pharmaceutically acceptable acid addition salts thereof due to their high level of activity. The former sulfamide is particularly preferred since its beta-adrenergic blocking action is relatively selective for cardiac and smooth muscle as opposed to the metabolic effects of anti-hyperglycemia and anti-hyperlactacidemia. A relative specificity for antagonism of the effects of beta-adrenergic agonists on the peripheral vasculature is displayed by this compound as compared to that on the heart. It is a potent anti-arrhythmic agent having 2.6 times the potency of procainamide and 1.3 times the potency of quinidine. The latter sulfamide exhibits the converse specificity in that it is a relatively stronger antagonist of the direct cardiac stimulatory effects evoked by beta-adrenergic agonists than of the peripheral vascular smooth muscle, and the hypotension caused thereby. The compounds of Formula I in which $R^4$ is hydrogen are useful as intermediates for the preparation of the compounds of Formula I wherein $R^4$ is lower alkyl. The compounds of Formula I wherein $R^1$ or $R^2$ is tert.-butyl are useful as intermediates for the preparation of compounds of Formula I wherein $R^1$ or $R^2$ is hydrogen.

DETAILED DESCRIPTION OF THE INVENTION

The starting materials for the preparation of the compounds of the present invention are para-aminoacetophenone, para-aminopropiophenone, and para-aminobutyrophenone when $R^3$ of Formula I is to be respectively hydrogen, methyl, or ethyl. These compounds are acylated with the appropriate $R^1R^2N$-substituted sulfamoyl halide or azide to yield the para-sulfamidophenone corresponding to the aminophenone starting material. The sulfamidophenone is then halogenated under conditions known to favor side chain halogenation as opposed to nuclear halogenation to provide the corresponding sulfamidophenacyl halide. The latter is then allowed to react with an N-benzyl-$R^4$-substituted amine to provide a compound of the formula

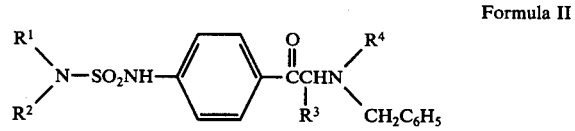

Formula II which on hydrogenation yields the compound of the present invention through cleavage of the N-benzyl group and reduction of the carbonyl group to a carbinol group.

Alternatively, the sulfamidophenacyl halide intermediate referred to above may be allowed to react with hexamethylenetetramine to provide a reaction complex which on hydrolysis in aqueous acid yields a sulfamidophenacylamine which after reduction of the carbonyl group to a carbinol group affords one of the compounds of the present invention wherein $R^1$, $R^2$, and $R^3$ are as defined in Formula I and $R^4$ is hydrogen. Other methods for the synthesis of primary amines from alkyl halides such as reaction with potassium phthalimide may also be used.

The primary amines (Formula I, $R^4$ is H) have the medicinal utilities referred to above and are also useful as intermediates for the production of other compounds of the present invention in which $R^4$ is lower alkyl having from 1 to 4 carbon atoms. The $R^4$ substitutents are introduced by conventional means such as by reductive alkylation using an alkylaldehyde or ketone having from 1 to 4 carbon atoms.

When it is desired to prepare one of the substances of the present invention wherein either $R^1$ or $R^2$ or both of them is a hydrogen atom, an N-tert.-butyl substituted sulfamoyl halide or azide is used as the acylating agent for the para-aminophenone in the first step of the process. This results in the production of a compound of the above formula in which $R^1$ or $R^2$ is tert.-butyl. The tert.-butyl group is readily removed by contacting the tert.-butylsulfamide with trifluoroacetic acid.

The depressor and beta-adrenergic blocking actions of the present substances may be demonstrated by conventional pharmacologic techniques. For example, the depressor response is evident when from 1 to 10 mg./kg. of body weight of one of the substances of Formula I. is injected intravenously into the anesthetized dog. The beta-adrenergic blocking action is evident in vitro when the isolated guinea pig trachea is cut into a spiral strip and suspended in a bath containing oxygenated Tyrode's solution and caused to relax by addition of a beta-adrenergic agonist such as isoproterenol to the bath. The relaxation brought about by the agonist is prevented by the prior addition of one of the present substances to the bath. The beta-adrenergic blocking action can be demonstrated in vivo in dogs anesthetized and surgically arranged for the recording of right ventricular contractile force, heart rate and blood pressure. beta-Adrenergic agonists such as isoproterenol cause an increase in heart rate and contractile force, and a decrease in blood pressure which can be prevented by prior treatment of the animal with one of the substances of the present invention.

The compounds of Formula I have exceedingly low toxicities. The $LD_{50}$ values measured in mice treated orally are in the range of 1 to 2 grams per kilogram of body weight. Effective intravenous doses in dogs are in the range of from 0.1 to 10 mg./kg. of body weight. For therapeutic use, they may be administered by the oral or parenteral routes in doses ranging from 0.1 to 100 mg./kg. of body weight.

The term "pharmaceutically acceptable" which has been used with reference to the acid addition and metal salts of the compounds of Formula I refers to such salts in which the anionic portion of the acid addition salt or the cationic portion of the metal salt does not contribute significantly to the toxicity of the compound nor interfere with its therapeutic and pharmaceutical application. Examples of pharmaceutically acceptable acid addition salts include the hydrochloride, hydrobromide, acetate, propionate, phosphate, nitrate, succinate, gluconate, mucate, sulfate, methanesulfonate, ethanesulfonate, p-toluenesulfonate, etc. salts. Pharmaceutically acceptable metal salts include the sodium, potassium, lithium, magnesium, calcium, barium, zinc, and aluminum salts. The sulfamide free bases of Formula I are also pharmaceutically acceptable forms.

DESCRIPTION OF SPECIFIC EMBODIMENTS

The nuclear magnetic spectral data reported below includes the chemical shifts ($\delta$) in parts per million, the multiplicity for that shift including the coupling constant (J value) when appropriate, and the relative area under the curve for each chemical shift which corresponds to the number of protons. The multiplicity symbols are: s, singlet; d, doublet; dd, doublet of doublets; bs, broad singlet; m, multiplet; and bm, broad multiplet. When deuterated dimethylsulfoxide (DMSO-d.) was used as solvent, the internal reference was tertramethylsilane. When deuterated water ($D_2O$) was used as solvent, it served as the reference (HDO peak at 4.70 ppm).

With respect to the infrared spectral data reported, only the principle peaks having specific structural significance are listed.

PROCEDURE 1.

N-(4-Acetylphenyl)-N',N'-dimethylsulfamide

Dimethylsulfamoyl chloride (14.4 g., 0.10 mole) is added dropwise to p-aminoacetophenone (13.5 g., 0.10 mole) in pyridine (60 ml.) at 10°–15° C. The mixture is stirred at room temperature overnight and then added to excess 6N HCl to give 14.1 g. (58%) of solid. The solid is dissolved in base, treated with charcoal, reprecipitated with dil. HCl, and recrystallized from water-isopropanol to give 8.9 g. (37%) of the above pure intermediate, m.p. 129°–130° C.

The foregoing procedure is adapted for use with other N,N-disubstituted sulfamoyl halides such as diethylsulfamoyl chloride, and methyl-tert.-butylsulfamoyl chloride. The following may be specifically prepared.

N-(4-Acetylphenyl)-N'-benzyl-N'-methylsulfamide.
4'-Acetyl-1-piperidinesulfonanilide. 4'-Acetyl-1-morpholinesulfonanilide
4'-Acetyl-1-pyrrolidinesulfonanilide
4'-Acetyl-1-thiamorpholinesulfonanilide.

Similarly, p-aminopropiophenone and p-aminobutyrophenone may be substituted for p-aminoacetophenone in Procedure 1 to provide N,N-dimethyl-N'-(4-propionylphenyl)sulfamide and N,N-dimethyl-N'-(4-N-butyrylphenyl)sulfamide respectively.

PROCEDURE 2

N-(4-Acetylphenyl)-N'-methylsulfamide

Methylsulfamoyl chloride (42.5 g., 0.33 mole) is added dropwise to a mixture of triethylamine (33.4 g., 0.33 mole) and p-aminoacetophenone (40.5 g., 0.30 mole )in ether (1.5 l.) at −50° C. The mixture is stirred at −50° C. and then allowed to warm to −10° C. The mixture is filtered to give a mixture of product and triethylamine hydrochloride. Washing with water and recrystallization from isopropanol furnishes 30.6 g. (40%) of the above pure intermediate, m.p. 159°–159.5° C. (dec.).

This method is particularly useful with N-monosubstituted sulfamoyl halides. Others which may advantageously be prepared in this fashion are N-(4-acetylphenyl)-N'-tert.-butylsulfamide, N-(4-acetylphenyl)-N'-ethylsulfamide, and N-(4-acetylphenyl)-N'-cyclopropylsulfamide.

PROCEDURE 3.

N-(4-Acetylphenyl)-N'-(4-tolyl) sulfamide

A solution of p-aminoacetophenone (3.65 g., 0.027 mole) in acetonitrile (50 ml.) is added dropwise to the triethylamine salt of p-toluenesulfamoylazide (0.027 mole) in acetonitrile (100 ml.). The solution is stirred for 2 days at room temperature and then concentrated in vacuo. The residue is dissolved in methylene chloride and, upon standing, yields 3 g. of the above intermediate. Another 2.2 g. may be obtained from the mother liquor. The combined crops are washed with water and recrystallized from isopropanol-heptane to yield the pure intermediate, m.p. 169.5°-170° C. (dec.).

Other arylsulfamoyl azides may be substituted for p-toluenesulfamoylazide in the foregoing procedure. For example, benzenesulfamoylazide may be employed to provide N-(4-acetylphenyl)-N'-phenysulfamide.

PROCEDURE 4

N-[4-(Bromoacetyl)phenyl]-N'-tert.-butylsulfamide

A few drops of bromine (from a total of 10.3 g., 0.064 mole) is added to N-(4-acetylphenyl)-N'-tert.-butylsulfamide (17.3 g., 0.064 mole) in dioxane (200 ml.) solution at 15° C. and the solution is stirred until the color is discharged. The remainder of the bromine is added during 5 min. and the solution is stirred for an additional 10 min. thereafter. The solution is concentrated in vacuo and the residue triturated with isopropyl ether to give 20.7 g. (92%) of intermediate, recrystallized from isopropanol, m.p. 160.5°-161° C. (dec.)

This method is applicable to each of the other 4-acylphenylsulfamides mentioned in connection with the foregoing procedures. In the case of the propiophenone and butyrophenone intermediates, bromination takes place on the aliphatic carbon atom adjacent to the carbonyl group to yield N-[4-(α-bromporopionyl)phenyl]-N',N'-dimethylsulfamide, and N-[4-(α-bromobutyryl)-phenyl]-N',N'-dimethylsulfamide. Specifically, the following intermediates may be prepared by this method.

N-[4-(Bromoacetyl)phenyl]-N'-methylsulfamide
N-[4-(Bromoacetyl)phenyl]-N'-ethylsulfamide
N-[4-(Bromoacetyl)phenyl]-N'-cyclopropylsulfamide
N-Benzyl-N'-[4-(bromacetyl) phenyl]-N-methylsulfamide
4'-Bromoacetyl-1-piperidinesulfonanilide
4'-Bromoacetyl-1-morpholinesulfonanilide
4'-Bromoacetyl-1-pyrrolidinesulfonanilide
4'-Bromoacetyl-1-thiamorpholinesulfonanilide
N-[4-(Bromoacetyl)phenyl]-N'-(4-tolyl)sulfamide para-toluenesulfonate
N-[4-(Bromoacetyl)phenyl]-N'-phenylsulfamide
N-[4-(Bromoacetyl)phenyl]-N',N'-dimethylsulfamide

PROCEDURE 5

N,N-Dimethyl-N'-(4-glycylphenyl)sulfamide Hydrochloride

N-[4-(Bromoacetyl)phenyl]-N', N'-dimethylsulfamide (32 g., 0.10 mole) is added dropwise to a chloroform solution of hexamethylenetetramine (21.0 g., 0.15 mole) and the mixture is stirred overnight to give 42.6 g. of the complex. This is hydrolyzed by heating 0.5 hr. with 40 ml. conc. HCl and 500 ml. abs. ethanol. The mixture is cooled and the insoluble ammonium chloride is removed. The solution is concentrated in vacuo and the residue is triturated with isopropanol to give 27.3 g. of intermediate which is washed with water and recrystallized from methanol-isopropyl ether, m.p. 159-159.5° C. (dec.)

Procedure 5 is applicable to the other 4-bromacetylphenylsulfamide intermediates referred to in the foregoing procedures, and specifically the following may be prepared.

N-Benzyl-N-methyl -N'-(4-glycylphenyl)sulfamide para-toluenesulfonate
4'-Glycyl-1-piperidinesulfonanilide para-toluenesulfonate
4'-Glycyl-1-morpholinesulfonanilide para-toluenesulfonate
4'-Glycyl-1-pyrrolidinesulfonanilide para-toluenesulfonate
4'-Glycyl-1-thiamorpholinesulfonanilide para-toluenesulfonate
N-[4-(α-Aminopropionyl)phenyl]-N',N'-dimethylsulfamide
N-[4-(α-Aminobutyryl)phenyl]-N',N'-dimethylsulfamide.

PROCEDURE 6

N-[4-(N-benzyl-N-isopropylglycyl)phenyl]-N'-tert.-butylsulfamide Hydrobromide The intermediate of Procedure 4 (10.0 g., 0.029 mole) is added portion-wise to an acetone solution (100 ml.) of benzylisopropylamine (9.0 g., 0.06 mole). The mixture is stirred for 5 hr. and then diluted with ether (400 ml.) to precipitate 4.9 g. of insoluble by-product benzylisopropylamine hydrobromide which is filtered and discarded. The filtrate is acidified with ethanolic hydrogen bromide to yield 13 g. (89%) of desired intermediate recrystallized from 95% ethanol, m.p. 195.5°-196.5° C. (dec.).

The following substances are prepared in the fashion described in Procedure 6.

N-[4-(N-Benzyl-N-isopropylglycyl)phenyl]-N'-methylsulfamide hydrobromide.
N[4-(N-Benzyl-N-isopropylglycyl)phenyl]-N'-(4-tolyl) sulfamide para-toluenesulfonate
N-[4-(N-Benzyl-N-isopropylglycyl)phenyl]-N'-phenylsulfamide
N-[4-(N-Benzyl-N-isopropylglycyl)phenyl]sulfamide paratoluenesulfonate
N-[4-(N-Benzyl-N-isopropylglycyl)phenyl]-N'-ethylsulfamide hydrobromide
N-[4-(N-Benzyl-N-isopropylglycyl)phenyl]-N'-cyclopropylsulfamide hydrobromide By substitution of tert.-butylamine, sec.-butylamine, and cyclopropylamine for benzylpropylamine in the method of Procedure 6, N-[4-(N-tert.-butylglycyl)-phenyl]-N'-tert.-butylsulfamide hydrobromide, N-[4-(N-sec.-butylglycyl)phenyl]-N'-tert. -butylsulfamide hydrobromide, and N-[4-(N-cyclopropylglycyl)-phenyl]-N'-tert.-burylsulfamide hydrobromide are prepared.

PROCEDURE 7

N-(4-Bromoacetyl)phenylsulfamide.

N-(4-Bromoacetylphenyl)-N'-tert.-burtylsulfamide (7.6 g., 0.022 mole) is dissolved in 75 ml. of trifluoroacetic acid and the solution is stirred for 5 hr. The solvent is then evaporated to yield 6.2 g. (96%) of the desired intermediate, m.p. 160.5°-161° C. (dec.), after recrystallization from acetonitrile.

PROCEDURE 8

N-[4-(1-Hydroxy-2-isopropylaminoethyl)phenyl]-N'-methysulfamide Hydrobromide A suspension of N-[4-(N-benzyl-N-isopropylglycyl)-phenyl]-N'-methysulfamide hydrobromide, 8.2 g., (0.018 mole) in 100 ml. of 90% aqueous ethanol is hydrogenated over palladium-on-charcoal catalyst at atmospheric pressure. When absorportion of hydrogen has been completed, the catalyst is removed and the solvent is evaporated in vacuo to yield 6.1 g. of the desired product, recrystallized from ethanol-isopropyl ether, m.p. 166°–168° C. (corr.).

Anal. Found: C, 39.06; H, 6.02; N, 11.11 which corresponds to the molecular formula $C_{12}H_{21}N_3O_3S \cdot HBr$.

Nuclear magnetic resonance, DMSO-d., $\delta$(ppm): 1.31 [d (6.6Hz), 6H]; 2.58 [s, 3H]; 3.24 [m, 2H]; 3.49 [septet (6.6Hz), 1H]; 5.02 [dd (6.0, and 7.1Hz), 1H]; and 7.37 ]m, 4H].

Infrared (pelletized with KBr): 815, 1070, 1160, 1330, 1380, 1390, 1450, 1510, 1595, 2720, 2820, 2980, 3220, and 3280 cm$^{-1}$.

Listed below are a number of additional products which may be prepared according to Procedure 8. Along with the name of the product, the melting point, recrystallization solvent, and other characterizing data is given. The intermediate from which each was prepared is also listed.

N,N-Dimethyl-N'-[4-(2-amino-1-hydroxyethyl)-phenyl]sulfamide para-Toluenesulfonate Melting point, 182.5°–183.5° C. (dec.)(corr.); recrystallized from 95% ethanol-isopropyl ether. Anal. Found: C, 47.08; H, 5.84; N, 9.69; which corresponds to the molecular formula $C_{10}H_{17}N_3O_3 \cdot C_7H_8O_3S$.

Nuclear magnetic resonance, D$_2$O, $\delta$(ppm): 2.29 [s, 3H]; 2.74 [s, 6H]; 3.17 [m, 2H]; 4.95 [dd (5.4, 7.4Hz), 1H]; 7.37 [m, 8H].

Infrared (pelletized with KBr): 815, 1150, 1185, 1345, 1400, 1470, 1515, 1615, 2970, and 3180 cm$^{-1}$. Prepared from N,N-dimethyl-N'-(4-glcylphenyl)sulfamide hydrochloride.

N'-[4-(2-Amino-1-hydroxyethyl)phenyl]-N-benzyl-N-methylsulfamide para-Toluenesulfonate Melting point, 152°–153° C. (corr); recrystallized from isopropanol-isopropyl ether. Anal. Found: C, 54.66; H, 5.61; N, 8.26; which corresponds to the molecular formula $C_{16}H_{21}N_3O_3 \cdot C_7H_8O_3S$.

Nuclear magnetic resonance, DMSO-d., $\delta$(ppm): 2.30 [s, 3H]; 2.59 [s, 3H]; 2.93 [m, 2H]; 4.27 [s, 2H]; 4.79 [m, 1H]; 6.02 [bs, 1H]; 7.32 [m, 16H].

Infared (pelletized with KBr): 690, 770, 820, 1130, 1160, 1220, 1340, 1520, 1620, 3100 cm$^{-1}$. Prepared from N-benzyl-N'-(4-glycylphenyl)-N-methylsulfamide para-toluenesulfonate.

4'-(2-Amino-1-hydroxyethyl)-1-piperidinesulfonanilide paratoluenesulfonate

Melting point, 168°–169° C. (dec.)(corr.), recrystallized from 95% ethanol-isopropyl ether. Anal. Found: C, 51.04; H, 6.19; N, 13.40; which corresponds to the molecular formula $C_{13}H_{21}N_3O_3O_3S \cdot C_7H_8O_3S$.

Nuclear magnetic resonance, DMSO-d$_6$, $\delta$(ppm): 1.43 [m, 6H]; 2.29 [s, 3H]; 3.09 [m, 6H]; 4.76 [m, 1H]; 5.93 [bs, 1H]; 7.33 [m, 8H]; 7.90 [bs, 3H]; 6.17 [s, 1H].

Infared (pelletized with KBr): 810, 1230–1120, 1340, 1510, 1610, 2860, 2940, 3140, 3300 cm.$^{-1}$. Prepared from 4-glycyl-1-piperidinesulfonanilide para-toluenesulfonate.

N-tert.-Butyl-N'-[4-(1-hydroxy-2-isopropylaminoethyl)phenyl]-sulfamide Hydrobromide Melting point 182° C. (dec.)(corr.), recrystallized from 95% ethanol. Anal. Found: C, 44.20; H, 6.84; N, 10.11; which corresponds to the molecular formula $C_{15}H_{27}N_3O_3S \cdot HBr$.

Nuclear magnetic resonance, D$_2$O, $\delta$(ppm): 1.18 [s, 9H]; 1.29 [d (6.6Hz), 6H]; 3.23 [m, 2H]; 3.48 [septet (6.6Hz), 1H]; 5.00 [dd (6.0, 7.2Hz), 1H]; 7.51 [m, 4H].

Infrared (pelletized with KBr): 840, 1145, 1330, 1395, 1520, 1615, 2800, 2980, 3160, 3300 cm$^{-1}$. Prepared from N-[4-(N-benzyl-N-isopropylglycyl)phenyl]-N'-tert.-butylsulfamide hydrobromide.

N-[4-(1-Hydroxy-2-isopropylaminoethyl)phenyl]sulfamide para-Toluenesulfonate Melting point 159°–160° C. (corr.), recrystallized from absolute ethanol-ispropyl ether. Anal. Found: C, 48.79; H, 6.18; N, 9.34; which corresponds to the molecular formula $C_{11}H_{19}N_3O_3S \cdot C_7H_8O_3S$.

Nuclear magnetic resonance, DMSO-d$_6$, $\delta$(ppm): [1.23 d(6.5Hz), 6H]; 2.30 [s, 3H]; 3.10 [m, 3H]; 4.85 [m, 1H]; 6.04 [bs, 1H]; 7.30 [m, 10H]; 9.25 [bs, 2H]; 9.50 [bs, 1H].

Infrared (pelletized with KBr): 820, 1160, 1330, 1400, 1520, 1620, 3160, 3230 cm$^{-1}$. Prepared from N- 4-(N-benzyl-N-isopropylglycyl)-phenyl sulfamide para-toluenesulfonate.

N-[4-(1-Hydroxy-2-isopropylaminoethyl)phenyl]-N'-(4-tolyl)-sulfamide para-Toluenesulfonate Melting point 164.5°–165.5° C. (corr.) recrystallized from absolute ethanol. Anal. Found: C, 56.11; H, 6.11; N, 7.63; which corresponds to the molecular formula $C_{18}H_{25}N_3O_3S \cdot C_7H_8O_2S$.

Nuclear magnetic resonance, DMSO-d$_6$, $\delta$(ppm): 1.22 [d (6.5Hz), 6H]; 2.21 [s, 3H]; 2.30 [s, 3H]; 3.15 [m, 3H]; 4.85 [m, 1H]; 6.05 [bs, 1H]; 7.30 [m, 12H]; 9.83 [bm, 4H].

Infrared (pelletized with KBr): 820, 1160, 1220, 1340, 1400, 1520, 1620, 2870, 2960, 3180 cm.$^{-1}$. Prepared from N-[4-(N-benzyl-N-isopropylgylcyl)phenyl]-N'-(4-tolyl)sulfamide para-toluenesulfonate.

Procedure 8 is also applicable to the preparation of N,N-dimethyl-N'-[4-(1-hydroxy-2-aminopropyl)-phenyl]sulfamide, and N,N-dimethyl-N'-[4-(1-hydroxy-2-aminobutyl)phenyl]sulfamide respectively from N-[4-(α-aminopropionyl)phenyl]-N',N'-dimethylsulfamide, and N-[4-(α-aminobutyryl)phenyl]-N',N'-dimethylsulfamide. Similarly, N-[4-(1-hydroxy-2-isopropylaminoethyl)phenyl]-N'-phenylsulfamide may be prepared from N-[4-(N-benzyl-N-isopropylglycyl)phenyl]-N'-phenylsulfamide.

Other sulfamidophenethanolamines which may be prepared by Procedure 8 from intermediates described herein are:

4'-(2-Amino-1-hydroxyethyl)-1-morpholinesulfonanilide para-toluenesulfonate

4'-(2-Amino-1-hydroxyethyl)-1-pyrrolidinesulfonanilide para-toluenesulfonate

4'-(2-Amino-1-hydroxyethyl)-1-thiamorpholine para-toluenesulfonate

N-tert.-Butyl-N'-[4-(1-hydroxy-2-cyclopropylaminoethyl)phenyl]-sulfamide hydrobromide N-tert.-Butyl-N'-[4-(1-hydroxy-2-tert.-butylaminoethyl)phenyl]-sulfamide hydrobromide N-ter.-Butyl-N'-[4-(1-hydroxy-2-sec.-butylaminoethyl)phenyl]-sulfamide hydrobromide Procedure 9

N-Benzyl-N'-[4-(1-hydroxy-2-isopropylaminoethyl)phenyl]-N:methysulfamide

N'-[4-(2-Amino-1-hydroxyethyl)phenyl]-N-benzyl-N-methylsulfamide para-toluenesulfonate, 0.021 mole, is converted to the free base by treatment with aqueous sodium hydroxide and extraction with ether. The ether extract is evaporated and the residue is dissolved in 100 ml. of ethanol and treated with 0.021 mole of acetic acid thus providing the acetate salt of the starting material. Acetone, 0.06 mole, is added to the solution which is then reduced at a pressure of 45 psig. with hydrogen over a platinum oxide catalyst. When hydrogen absorption ceases, the catalyst is removed and the reaction solvent is distilled in vacuo. The residue is treated with aqueous sodium bicarbonate and the mixture extracted with methylene chloride. The dried extracts are concentrated in vacuo and the residue triturated with ether to yield 6.2 g. of the desired product which is crystallized from isopropanol:isopropyl ether, m.p. 131°–134.5° C. (corr.).

Anal. Found: C, 60.44; H, 7.44; N, 11.17.

Nuclear magnetic resonance, DMSO-d$_6$, δ(ppm): 0.99 ( d (6.2 Hz), 6H]; 2.60 [s, 3H]; 2.68 [m, 3H]; 4.26 [s, 2H]; 3.77 [dd (6.0, 7.0Hz), 1H]; 5.20 [bs, 3H]; 7.30 [m, 9H].

Infrared (pelletized with KBr): 695, 765, 840, 1150, 1340, 1380, 1395, 1452, 1510, 1610, 2860, 2920, 3120, 3280 cm.$^{-1}$.

The following substances were prepared according to Procedure 9. Along with the name of the product, the melting point, recrystallization solvent, and other characterizing data is listed. The intermediate from which each was prepared with also identified.

4'-(2-Isopropylamino-1-hydroxyethyl)-1-piperidinesulfonilide Hydrochloride.

Melting point 176°–176.5° C. (corr.) recrystallized from isopropanol-95% ethanol-isopropyl ether. Anal. Found: C, 50.56; H, 7.35; N, 11.07.

Nuclear magnetic resonance, DMSO-d$_6$, δ(ppm): 1.28 [d, (6.5Hz)]; 1.43 [m, 12H when combined with preceding shift]; 3.09 [m, 7H]; 5.00 [m, 1H]; 6.08 [bs, 1H]; 7.28 [m, 4H]; 9.00 [bs, 1H]; 9.60 [bs, 1H]; 10.20 [s, 1H];

Infrared (pelletized with KBr): 840, 1055, 1145, 1340, 1405, 1470, 1520, 1620, 2860, 2850 cm.$^{-1}$. Prepared from 4'-(2-amino-1-hydroxyethyl)-1-piperidinesulfonanilide para-toluenesulfonate.

N,N-Dimethyl-N'-[4-(1-hydroxy-2-isopropylaminoethyl)phenyl]-sulfamide Hydrochloride Melting point 182°–183.5° C. (corr.), recrystallized from 95% ethanol-ethyl ether. Anal. Found: C, 45.94; H, 7.09; N, 12.16.

Nuclear magnetic resonance, D$_2$O, δ(ppm): 1.36 ( d (6.5 Hz), 6H]; 2.80 [s, 6H]; 3.45 [m, 3H]; 5.07 [dd (6.0, 7.1 Hz), 1H]; 7.40 [m, 4H].

Infrared (pelletized with KBr): 840, 1145, 1335, 1400, 1470, 1520, 1620, 2980, 3140 cm.$^{-1}$. Prepared from N,N-dimethyl-N'-[4-(2-amino-1-hydroxyethyl)phenyl]sulfamide para-toluenesulfonate.

What is claimed is:

1. The method for inhibiting beta-adrenergic activity in a mammalian host having a disease state resulting from excessive activation of the beta-adrenergic receptors which comprises administering to said host a nontoxic effective adrenergic beta-receptor inhibiting dose of a compound selected from a group consisting of

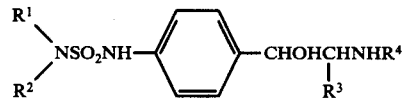

wherein:
R$^1$ is hydrogen, lower alkyl having from 1 to 4 carbon atoms cyclopropyl, phenyl, or tolyl;
R$^2$ is hydrogen, lower alkyl having from 1 to 4 carbon atoms, cyclopropyl or benzyl; or
R$^1$ and R$^2$ are joined to form with the nitrogen atoms to which they are attached the 1-piperidyl group;
R$^3$ is hydrogen, methyl, or ethyl; and
R$^4$ is hydrogen, cyclopropyl, or lower alkyl having from 1 to 4 carbon atoms,
and the pharmaceutically acceptable acid addition and metal salts thereof.

2. The process of claim 1 wherein said dose is administered by the oral or parenteral routes within the range of 0.1 to 100 mg./kg. of body weight of said host.

3. The process of claim 1 wherein said disease state is selected from the group consisting of angina pectoris, cardiac arrhythmia, hypertension, anxiety neurosis, hyperlactic acidemia, hyperglycemia, and ketosis.

4. The process of claim 1 wherein said compound is N,N-dimethyl-N'-[4-(1-hydroxy-2-isopropylaminoethyl)phenyl]sulfamide or a pharamceutically acceptable acid additon of metal salt thereof.

5. The process of claim 1 wherein said compond is N-[4-(1-hydroxy-2-isopropylaminoethyl)phenyl]sulfamide or pharmaceutically acceptable acid addition or metal salt thereof.

6. The process of claim 4 wherein said disease state is selected from the group consisting of angina pectoris, cardiac arrhythmia, and hypertension.

7. The process of claim 5 wherein said disease state is selected from the group consisting of angina pectoris, cardiac anhythmia, and hypertension.

* * * * *